United States Patent [19]

Fisher et al.

[11] Patent Number: 5,106,831
[45] Date of Patent: * Apr. 21, 1992

[54] PHARMACEUTICAL COMPOSITION COMPRISING A SPIRO OXATHIOLON/QUINUCLIDINE AND METHOD OF TREATING SENILE DEMENTIA

[75] Inventors: Abraham Fisher, Holon; Ishai Karton, Ness-Ziona; Eliahu Heldman; Yona Grunfeld, both of Rehovot; Aharon Levy, Beit Hanan, all of Israel

[73] Assignee: State of Israel, represented by the Prime Minister's office, Israel Institute for Biological Research, Israel

[*] Notice: The portion of the term of this patent subsequent to Aug. 8, 2006 has been disclaimed.

[21] Appl. No.: 599,977

[22] Filed: Oct. 19, 1990

Related U.S. Application Data

[60] Division of Ser. No. 339,888, Apr. 18, 1989, Pat. No. 4,981,858, which is a continuation of Ser. No. 84,799, Aug. 13, 1987, abandoned.

[51] Int. Cl.$^5$ ............... A01N 37/18; A01N 43/42; A01N 57/26; A61K 37/00
[52] U.S. Cl. ..................... 514/2; 514/278; 514/78; 514/11
[58] Field of Search ............. 514/278, 2, 78, 11

[56] References Cited

U.S. PATENT DOCUMENTS 4,855,290  8/1989  Fisher ..................... 514/278

Primary Examiner—Frederick E. Waddell
Assistant Examiner—Gregory Hook
Attorney, Agent, or Firm—Sterne, Kessler, Goldstein & Fox

[57] ABSTRACT

A pharmaceutical composition is disclosed comprising (−)-cis-2-methylspiro(1,3-oxathiolan-5,3')quinuclidine, and/or the pharmaceutically compatible acid addition salts thereof, together with at least one of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor. Also disclosed is a method for treating senile dementia of Alzheimer's type, which comprises coadministering to a patient in need thereof an effective dose of the spiro compound together with at least one other compound selected from those listed above.

18 Claims, No Drawings

PHARMACEUTICAL COMPOSITION COMPRISING A SPIRO OXATHIOLON/QUINUCLIDINE AND METHOD OF TREATING SENILE DEMENTIA

CROSS REFERENCE TO RELATED APPLICATIONS

The present application is a division of U.S. Pat. No. 4,981,858, issued Jan. 1, 1991, based on U.S. application Ser. No. 07/339,888, filed Apr. 18, 1989, a continuation application of U.S. application Ser. No. 07/084,799, filed Aug. 13, 1987, now abandoned.

FIELD OF THE INVENTION

The present invention relates to the optical isomers of a spiroquinuclidine derivative, to pharmaceutical compositions comprising such isomers, to a method for treating diseases of the central nervous system therewith and to a process for preparing said isomers.

BACKGROUND OF THE INVENTION

The present applicants were co-inventors of previous patent applications relating to novel spiro-derivatives of quinuclidine, see e.g. European Patent Appln. No. 0205247 A2, published Dec. 17, 1986, based on Israel Patent Applications Nos. 75166 filed May 10, 1985 and 77568 filed Jan. 10, 1986, and commonly assigned U.S. patent application Ser. No. 853,404 filed Apr. 18, 1986, the contents of which are incorporated herein by reference. These novel quinuclidine derivatives were found to possess central nervous system activity. The biological activity of the compound 2-methylspiro(1,3-oxathiolane-5',3)quinuclidine, which exists as geometrical cis- and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of pre-clinical tests that the cis-compound could be especially promising for the control of senile dementia of Alzheimer's type (SDAT).

In addition to the existence of geometrical isomerism, the compounds in question also possess a potential for optical isomerism, as will be appreciated by those skilled in the art. As is also known, however, such a potential is not always readily realized in practice. Moreover, in view of the promise of the geometrical isomers of the compound 2-methylspiro(1,3-oxathiolane-5',3)quinuclidine for the treatment of SDAT, it is evidently of interest to know the relative biological activity of such compounds. The relationship between the direction of rotation of the plane of polarized light by a particular optical isomer on the one hand, and its biological potency on the other, is not predictable with any degree of certainty.

Therefore, it is a principal object of the invention to provide optical isomers of 2-methylspiro(1,3-oxathiolane-5',3)quinuclidine. Further objects of the invention, and especially those which relate to the provision of useful pharmaceutical compositions and methods for the treatment of disease in mammals, will be apparent from the description which follows.

SUMMARY OF THE INVENTION

The present invention accordingly provides in one aspect, the individual optical isomers selected from the group consisting of (+)-cis-, (−)-cis-, (+)-trans- and (−)-trans-2-methylspiro(1,3-oxathiolan-5,3')quinuclidine, and especially such isomers in which the specific rotation has been determined. Preferably, such isomers are obtained in a highly pure state, more particularly having at least 95% optical purity.

The invention includes the acid addition salts of these individual optical isomers, and especially such addition salts which are pharmaceutically compatible.

Particular individual optical isomers provided in accordance with this aspect of the invention are the following:

(+)-cis-2-methylspiro(1,3-oxathiolan-5,3')quinuclidine, the free base in ethanol having $[\alpha]^{20}$ about $+32\pm1$;

(−)-cis-2-methylspiro(1,3-oxathiolan-5,3')quinuclidine, the free base in ethanol having $[\alpha]^{20}$ about $-32\pm1$;

(+)-trans-2-methylspiro(1,3-oxathiolan-5,3')quinuclidine, the free base in ethanol having $[\alpha]^{20}$ about $+24\pm1.2$; and (−)-trans-2-methylspiro(1,3-oxathiolan-5,3')quinuclidine, the free base in ethanol having $[\alpha]^{20}$ about $-24\pm1.2$.

In another aspect, the invention provides a pharmaceutical composition which comprises at least one member selected from the group consisting of (+)-cis-, (−)-cis-, (+)-trans- and (−)-trans-2-methylspiro(1,3-oxathiolan-5,3')quinuclidine, or a pharmaceutically compatible acid addition salt thereof, together with an inert carrier or diluent. The composition may be, for example, in a form suitable for oral, rectal or parenteral administration, or for administration by insufflation or nasal spray. Alternatively, it may be in a form suitable for transdermal administration, and in this case it may comprise as an additional component, a low molecular weight fatty acid.

The expression "at least one member" or "at least one optical isomer", as used in the present specification and claims, defines one such member (i.e. optical isomer), and any mixture of two or more such members, except where such a mixture would constitute the cis- or trans-racemates per se. These racemates are of course described and claimed in the prior patent applications which have been mentioned above.

The pharmaceutical composition provided according to this aspect of the invention may conveniently be in unit dosage form. Suitably, the at least one optical isomer referred to above, or a pharmaceutically compatible acid addition salt thereof, may be present in an amount in the range of about 0.5 to about 500 mg., together with an inert carrier or diluent. This amount lies preferably within the range of about 5 to about 100 mg., more preferably within the range of about 10 to about 50 mg.

The presently preferred optical isomer provided in accordance with the present invention is (−)-cis-2-methylspiro (1,3-oxathiolan-5,3')quinuclidine, which appears to possess the highest desired biological potency of all the isomers. This (−)-cis-isomer may be used as the free base, or in the form of a pharmaceutically compatible acid addition salt thereof, and pharmaceutical compositions which contain this isomer preferably comprise additionally (for reasons which will become clearer infra) at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine or Nerve Growth Factor, and desirably also, an inert carrier or diluent.

In accordance with a further aspect of the invention, there is provided a method for treating diseases of the central nervous system in mammals, details of which will be described infra.

The invention also provides according to still a further aspect, a process for the preparation of at least one of the individual optical isomers described herein, which comprises treating a base selected from the group consisting of (±)-cis-2-methylspiro(1,3-oxathiolan-5,3')quinuclidine and (±)-trans-2-methylspiro(1,3-oxathiolan-5,3')quinuclidine with an amount of enantiomeric acid insufficient for stoichiometric reaction, and fractionating the precipitated salt until a fraction of desired optical purity is obtained. The mother liquors and the precipitate may be further processed as described below.

DETAILED DESCRIPTION OF THE INVENTION

The present inventors have found that when attempts are made to resolve either the cis- or the trans-2-methylspiro(1,3-oxathiolan-5,3')quinuclidine, by fractional crystallization using d- and l-tartaric acid, then in each case the respective enantiomers (+) and (−) are obtained. The total of four isomers exhausts all the possibilities, as may be seen from a consideration of the structural formulae in question [see, for example, Saunders et al, J. Med. Chem. 30: 969–75 (1987), the contents of which article are incorporated herein by reference, and in which article dioxolan analogues of the present compounds were prepared by a synthetic route followed by chromatographic separation, and not by optical resolution of racemates as in the present invention].

According to the optical resolution process of the present invention, a base selected from the group consisting of (±)-cis-2-methylspiro(1,3-oxathiolan-5,3')quinuclidine and (±)-trans-2-methylspiro(1,3-oxathiolan-5,3')quinuclidine is treated with an amount of enantiomeric acid insufficient for stoichiometric reaction, and the precipitated salt is fractionated until a fraction of desired optical purity is obtained. The enantiomeric acid may be e.g. L- or D-tartaric acid, or/and L- or D-mandelic acid, although other optically active acids may be used for the same purpose, as of course is well known in the art. The amount of enantiomeric acid may be e.g. about 50% of the equimolar amount which would be necessary to react with all the racemic base present. The reaction may be carried out in an organic solvent such as ethanol. As is also known, it is within the competence of one skilled in the art to select a suitable solvent for the purpose. The mode of fractionation is conveniently fractional crystallization. The present inventors have found that a small number of crystallizations (e.g. two) will normally give a product of high optical purity, e.g. 95% or better.

The mother liquor or liquors from the salt forming reaction and/or recrystallization may be basified and the residual base may then be treated with the enantiomer of the enantiomeric acid originally used, and the precipitated salt is again fractionated until a fraction of desired optical purity is obtained. This stage will give a salt of the base, wherein the latter has the opposite optical rotation of the base present in the salt obtained in the first stage of the salt forming reaction.

In order to obtain the desired enantiomeric bases, either or both salts formed in the first and second stages just described may be treated with a base such as an alkali metal hydroxide. There will thus be obtained an enantiomeric base selected from the group consisting of (+)- and (−)-cis-2-methylspiro(1,3-oxathiolan-5,3')quinuclidine and (+)- and (−)-trans-2-methylspiro(1,3-oxathiolan-5,3')quinuclidine. Such an enantiomeric base may of course be treated with an acid (especially a pharmaceutically compatible acid) to form an acid addition salt thereof. Examples of suitable such acids are described below.

The individual optical isomers of the present invention are muscarinic agonists with a high specificity for the central nervous system. They are highly specific for a subpopulation of muscarinic receptors, namely pirenzepine-sensitive M1 receptors. Due to their pharmacological properties, these compounds can activate central cholinergic functions under conditions where the cholinergic system is hypofunctional. These compounds [and especially the (−)-cis-isomer] can therefore be utilized for the treatment of conditions such as presenile dementia, senile dementia of Alzheimer's type (SDAT), mixed Alzheimer's and Parkinson's disease, tardive dyskinesia, acute confusion conditions, hyperkinesia, mania, Pick's disease, Huntington's chorea, Friedrich's ataxia, Down's syndrome, Gilles de la Tourette disease, post encephalitic amnesic syndrome, alcohol withdrawal symptoms, and progressive supranuclear palsy, because all of these disease states are disturbances in which a central cholinergic hypofunction has been implicated at least to a certain extent.

These compounds [and especially the (−)-cis-isomer] would appear to be of value for the treatment of SDAT. Thus, in SDAT patients, the (−)-cis-isomer in particular can be used in combination with anticholinesterase inhibitors such as physostigmine or tetrahydroaminoacridine; in combination with acetylcholine precursors such as choline or lecithin; in addition to "nootropic" drugs such as piracetam, aniracetam, oxiracetam or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin; in combination with a peripheral antimuscarinic agent (such as pirenzepine, N-methylatropine or N-butylscopolamine) to counteract peripheral adverse effects that might be expected at high doses, such as salivation, diarrhea, gastric secretion or vomiting, or in combination with transdermal scopolamine such as Scopoderm ® to counteract nausea and/or vomiting; in combination with an adrenergic agonist (clonidine or quanfamicine) in order to alleviate both the cognitive and other impairments associated with a mixed cholinergic-nonadrenergic deficiency in SDAT; in combination with Nerve Growth Factor (NGF, which is administered either by a nasal spray or intracerebroventicularly).

The (−)-cis-isomer of the present invention, with or without the aforementioned other active substances, can be administered for example, by way of injection in a suitable diluent or carrier, per os, rectally in the form of suppositories, by way of insufflation or nasal spray, by infusion or transdermally in a suitable vehicle with or without physostigmine, for example by using the device which is the subject of Israel Patent Application No. 72684 (vide infra). This compound may also be used in disturbances where cholinergic underactivity is induced by drugs.

The (−)-cis-isomer, either by itself or in admixture with one or more other of the optical isomers of the invention, is also of use for the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyryl-cholinesterase. This compound may also be used for the treatment of peripheral cholinergic disorders such as myasthenia gravis, urinary bladder dysfunctions, Adi's disease and Eaton-Lambret disease.

The individual optical isomers of the present invention form stable addition salts with organic and inorganic acids. While for therapeutic purposes such salts should be pharmaceutically compatible, nevertheless it may be convenient, as for example for the purpose of isolation, to employ acid addition salts which are not pharmaceutically compatible, and the invention includes also the latter kind of acid addition salts. As will be obvious to those skilled in the art, the free bases may be converted to acid addition salts by reaction with the appropriate acid, and the salts may be converted by reaction with a base (e.g., an alkali metal hydroxide in aqueous solution) to the corresponding free bases.

The term "pharmaceutically compatible acid addition salt" as used herein refers to a combination of said quinuclidine derivative with relatively non-toxic inorganic or organic acids. Illustrative only of suitable acids are sulfuric, phosphoric, hydrochloric, hydrobromic, hydriodic, sulfamic, methanesulfonic, benzenesulfonic, para-toluenesulfonic, acetic, lactic, succinic, maleic, tartaric, citric, gluconic, ascorbic, benzoic and cinnamic acids.

Where the term "pharmaceutical composition" is used in the present specification and claims, this is to be understood in the sense that it may be suitable for human and/or veterinary treatment. In the pharmaceutical compositions of the invention, suitable pharmaceutical carriers and diluents, which comprise both solids and liquids, may, by way of example only, be selected from corn starch, lactose, calcium phosphate, stearic acid, polyethylene glycol, water, sesame seed oil, peanut oil, propylene glycol, and so forth. This composition may be in a form suitable for oral, rectal or parenteral administration, or for administration by insufflation or nasal spray, or in particular it may be in a form suitable for transdermal administration, and in any event the composition may be in unit dosage form. Exemplary compositions may take the form of tablets, powder, granules, capsules, suspensions, solutions, suppositories, elixirs, ointments and the like.

When the pharmaceutical composition is to be administered transdermally, it is preferred to utilize the drug delivery system according to Israel Patent Application No. 72684, although transdermal administration in accordance with the invention is not of course limited to this system. Thus, as mentioned previously, the pharmaceutical compositions of the invention adapted for transdermal administration may comprise as an additional ingredient, a low molecular weight fatty acid.

For the reasons noted hereinbefore, such a composition may contain as a further ingredient or ingredients, one or more compounds selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butyl-scopolamine, scopolamine, clonidine, quanfamicine or Nerve Growth Factor.

As has already been indicated, the present invention provides a method for treating diseases of the central nervous system in mammals (especially diseases due to a deficiency in the central cholinergic system), which comprises administering to the mammal, preferably in the form of a pharmaceutical composition as described above, at least one member selected from the group consisting of (+)-cis-, (−)-cis-, (+)-trans- and (−)-trans-2-methylspiro(1,3-oxathiolan-5,3')quinuclidine, or a pharmaceutically compatible acid addition salt thereof. According to an embodiment of this aspect of the invention, a method for treating senile dementia of Alzheimer's type comprises administering to a patient the compound (−)-cis-2-methylspiro(1,3-oxathiolan-5,3')quinuclidine, or a pharmaceutically compatible acid addition salt thereof, and preferably in the form of a pharmaceutical composition, as described above. For this purpose, the (−)-cis-isomer may be administered via the oral route in an amount which lies within the range of about 0.1 to about 60 mg./kg., preferably about 0.5 to about 10 mg./kg. body weight, more preferably about 1 to about 5 mg./kg. body weight. within the range of about 1 to about 5 mg./kg. body weight. On the other hand, this compound may be administered via the parenteral route (which includes, for example, intramuscular, intravenous and subcutaneous administration) in an amount which lies within the range of about 0.01 to about 40 mg./kg., preferably about 0.05 to about 5 mg./kg. body weight, more preferably about 0.1 to about 2 mg./kg. body weight.

In prescribing a particular form and rate of administration, the physician will of course take into consideration the usual factors such as the severity of the symptoms, the physical circumstances of the patient, and so forth.

Taking into account the usual weight ranges of patients, the foregoing dosage ranges, and the possibility that it may be desirable to administer multiple rather than single doses, pharmaceutical compositions in accordance with the invention which are adapted for oral or parenteral administration, may contain the active ingredient [and especially the (−)-cis-isomer of the invention], in an amount (for example) in the range of about 0.5 to about 500 mg., preferably about 5 to about 100 mg., more preferably in the range of about 10 to about 50 mg.

For the purpose of definition, it is intended that the expression "method for the treatment of diseases of the central nervous system", and like expressions, throughout the specification and claims, be taken to include a method for the prevention of drug-induced diseases of the central nervous system.

The invention will be illustrated by the following non-limitative Examples.

EXAMPLE I

Separation of the individual enantiomers of cis- and trans-2-methylspiro(1,3-oxathiolan-5,3')quinuclidine Cis-2-methylspiro(1,3-oxathiolan-5,3')quinuclidine as the free base (37.5 g., 0.188 mole) and L-tartaric acid (14.08 g., 0.094 mole) were placed in a 2 liter flask, absolute ethanol (1120 g.) was added, the mixture was refluxed for 10 minutes and then allowed to stand overnight. The resulting precipitate was filtered off and recrystallized from absolute ethanol. The solid product was basified and reprecipitated as the hydrochloride salt (yield: 11.7 g., 26%); it had m.p. 198°-200° C. and $[\alpha]^{20} + 32 \pm 1$ (free base in ethanol).

The mother liquor was evaporated, basified and treated with D-tartaric acid in the same manner. After two recrystallizations, the resulting tartrate was basified and reprecipitated as the hydrochloride salt (yield: 14.7 g., 33.2%); it had m.p. 198°-200° C. and $[\alpha]^{20} - 32 \pm 1$ (free base in ethanol).

The following properties apply to each enantiomer. $R_f$(TLC, neutral alumina, chloroform) 0.7. NMR spectrum using pure 2,2,2-trifluoro-1-(9-anthryl)ethanol ($C_6D_6$) shows the presence of a single enantiomer (>95% optical purity). The NMR spectrum of the hydrochloride salt in $CDCl_3$ is identical to that of the ($\pm$)-cis-isomer hydrochloride.

By a similar procedure to the above there were obtained:

(−)-trans-2-methylspiro(1,3-oxathiolan-5,3′)quinuclidine, the free base in ethanol having $[\alpha]^{20} - 24 \pm 1.2$ and (+)-trans-2-methylspiro(1,3-oxathiolan-5,3′)quinuclidine, the free base in ethanol having $[\alpha]^{20} + 24 \pm 1.2$.

In the latter instance, there was used additionally l-mandelic acid and the l-mandelate was recrystallized from ethyl acetate.

EXAMPLE II

Biological Testing of the Isolated Enantiomers

The $LD_{50}$ in mice of (+)-, (−) and [for comparison] ($\pm$)-cis-2-methylspiro(1,3-oxathiolan-5,3′)quinuclidine (HCl salts) is shown in Table 1. There are no significant differences in the toxicity of the tested compounds.

TABLE 1

| | | $LD_{50}$ (mg./kg.) | 95% confidence limits |
|---|---|---|---|
| ($\pm$)-isomer | male | 45 | 40.9–49.6 |
| | female | 40.8 | 36.6–45 |
| (+)-isomer | male | 39.1 | 35.6–42.6 |
| | female | 45.0 | 33.8–56.3 |
| (−)-isomer | male | 35 | 26.3–43.8 |
| | female | 40 | 30–50 |

The potency of putative cholinergic compounds in displacing from rat forebrain homogenates the following $^3$H-labelled compounds, namely, $^3$H-quinuclidinyl benzilate ($^3$H-QNB; a non-selective $M_1$ and $M_2$ antagonist), $^3$H-Pirenzepine ($^3$H-PZ; a selective $M_1$ antagonist) and $^3$H-cis-dioxolane($^3$H-CD, a non-selective $M_1$ and $M_2$ agonist), is shown in Table 2. Included in this study for comparative purposes are Oxotremorine (mainly an $M_2$ agonist), McN-A-343 (mainly an $M_1$ agonist), and ($\pm$)-cis-and trans-2-methylspiro(1,3-oxathiolan-5,3′)quinuclidine.

TABLE 2

| Compd. tested # | (a) $^3$Ki(H-PZ) fM | (b) $^3$Ki(H-QNB) fM | (c) $^3$Ki(H-CD) fM | (d) a:b | (e) a:c |
|---|---|---|---|---|---|
| 1 | 0.6 ± 0.2 (4) | 1.7 ± 0.3 (8) | 9.6 ± 4.2 (2)* | 0.35 | 625 |
| 2 | 4.9 ± 1.9 (4) | 14.2 ± 1.41 (3) | 0.4 ± 0.1 (4) | 0.35 | 12.25 |
| 3 | 14.6 ± 2.9 (4) | 24.7 ± 2.3 (8) | 1.8 ± 0.1 (2) | 0.59 | 8.1 |
| 4 | 0.6 ± 0.15 (7) | 6.3 ± 1.0 (15) | 0.45 ± 0.18 (4) | 0.10 | 1.4 |
| 5 | 1.1 ± 0.3 (3) | 3.5 ± 1.5 (3) | 0.21 ± 0.06 (2) | 0.32 | 5.2 |
| 6 | 9.6 ± 1.8 (3) | 36.4 ± 8 (3) | 7.5 (1) | 0.26 | 1.3 |

Key to TABLE 2:
$K_i = IC_{50}/(1 + C/K_D)$, where C is the concentration of the radioactive ligand and $K_D$ is the dissociation constant thereof.
compounds tested -
1 = Oxotremorine (*expressed in M × 10$^{-10}$)
2 = McN-A-343
3 = ($\pm$)-trans-isomer
4 = ($\pm$)-cis-isomer
5 = (−)-cis-isomer
6 = (+)-cis-isomer

DISCUSSION OF TABLE 2

From Table 2, it is evident that the ($\pm$)-cis-isomer has the highest $M_1$ selectivity followed by its (−) and (+) enantiomers. The (−)-cis-enantiomer is 2.2 times more potent in $^3$H-QNB displacement than its racemate. Moreover, the ($\pm$)-cis-isomer is the most selective $M_1$ agonist, being more selective than the prototype $M_1$ agonist McN-A-343. As can be seen from the ratios Ki($^3$H-PZ):Ki($^3$H-CD) and Ki($^3$H-PZ):Ki$^3$H-QNB) in columns (d) and (e) of the Table, the structurally rigid compounds of the present invention showed higher selectivity towards $M_1$ receptors than McN-A-343 or Oxotremorine. However, there were some apparent discrepancies between the order of the ratios Ki($^3$H-PZ):Ki($^3$H-CD) and Ki($^3$H-PZ):Ki($^3$H-QNB) among the tested compounds, especially in regard to Oxotremorine, the ($\pm$)-trans-isomer and McN-A-343. While the order of the ratios Ki($^3$H-PZ):Ki($^3$H-CD) for these three compounds was oxotremorine > McN-A-343 > ($\pm$)-trans-isomer, the order of the ratios Ki($^3$H-PZ):Ki($^3$H-QNB) was McN-A-343 > ($\pm$)-trans-isomer > oxotremorine. These ratios are indices for the relative selectivity of the tested compounds towards $M_1$ as against $M_2$ receptors. It is not clear why in one test, oxotremorine showed the weakest relative affinity towards $M_1$ binding sites [Ki($^3$H-PZ):Ki($^3$H-CD)] whereas in the other test its relative affinity towards the $M_1$ binding sites was relatively stronger than McN-A-343 and the ($\pm$)-trans-isomer [Ki($^3$H-PZ):Ki($^3$H-QNB)]. One explanation of this phenomenon is that since the affinity of oxotremorine towards all muscarinic receptors is greater than those of the weaker agonists McN-A-343 or the ($\pm$)-trans-isomer [Watson et al, JPET 237: 411–418 (1986)], then lower concentrations of oxotremorine are needed to displace both $^3$H-PZ and $^3$H-QNB from forebrain homogenate, especially $^3$H-PZ which possesses lower affinity towards muscarinic receptors than $^3$H-QNB. Thus, in principle, strong agonists will yield a lower Ki($^3$H-PZ):Ki($^3$H-QNB) ratio than weak agonists, without taking into consideration the selectivity of the selected ligands. On the other hand, the $K_D$ of $^3$H-PZ is similar to that of $^3$H-CD and therefore weak and strong agonists should behave similarly in displacing these labelled ligands, unless their selectivity towards one receptor subpopulation is different. Therefore, the ratio $Ki(^3H\text{-}PZ):Ki(^3H\text{-}CD)$ should represent more accurately the relative affinities towards $M_1$ receptors. Indeed, the order of these ratios for the compounds tested is consistent with the order found for the ratios $IC_{50}(FB):IC_{50}(CER)$ which also serves as an index for $M_1$ versus $M_2$ selectivity, namely, ($\pm$)-cis-isomer>($\pm$)-trans-isomer>oxotremorine (FB=forebrain, which contains mainly $M_1$ receptors; CER=cerebellum, which contains mainly $M_2$ receptors).

Table 3 shows the results of a study of isolated guinea pig ileum induced contraction. From this Table also, it is evident that the (−)-cis-isomer of the present invention is twice as active as the corresponding racemate, while the (+)-cis-isomer lacks significant agonist activity.

TABLE 3

| Compound | EC50 (M) | type of activity |
| --- | --- | --- |
| Acetylcholine | $5 \times 10^{-8}$ | agonist |
| ($\pm$)-cis-isomer | $3 \times 10^{-6}$ | agonist |
| (−)-cis-isomer | $1.5 \times 10^{-6}$ | agonist |
| (+)-cis-isomer | $>10^{-5}$ | inactive as agonist |
| ($\pm$)-trans-isomer | $>10^{-5}$ | agonist |

BEHAVIORAL EXPERIMENTS

Ethylcholine aziridinium ion (hereinafter denoted AF64A) is a selective presynaptic cholinergic neurotoxin, which on intracerebroventricular injection in rats induces persistent cholinergic hypofunction that mimics the cortical and hippocampal cholinergic deficiency and the cognitive impairments reported in SDAT. Accordingly, the possibility of reversal of the AF64A-induced effects by (−)- and [for comparison] ($\pm$)-cis-2-methylspiro(1,3-oxathiolan-5,3')quinuclidine in the passive avoidance task was studied. In this experiment, the results of which are reported in Table 4, we investigated the effect of these substances (0.2 mg./kg., per os) on the retention after 72 hours of an inhibitory learning (passive avoidance-step through) task in AF64A and saline-injected rats, using a post-training drug treatment paradigm. The surgery carried out on the test animals (Sprague-Dawley rats raised by Charles River) was similar to that described in our prior published European Patent Application No. 0205247. The behavioral studies were performed one month after surgery.

BEHAVIORAL TESTING

The behavioral testing procedure comprised two phases, 1 and 2. In a pretest training procedure each rat was individually placed in a small lighted front compartment of a two-compartment box. After a 60 secs. familiarization/adaptation period, the door separating the two compartments was opened and a clock activated. The rat's latency to enter the large dark compartment of the box (to step-through) was measured. Immediately following entry into the dark compartment, the rat was subjected to an inescapable scrambled foot shock applied to the grid floor (0.6 mA for 3 secs.). Sixty secs. after the termination of the shock, at the end of the training procedure, the rat was removed from the dark compartment and double distilled water, (−)- and ($\pm$)-cis-2-methylspiro(1,3-oxathiolan-5,3')quinuclidine were administered per os. Rats were then returned to their home cage. Retention of the passive avoidance task was measured 24 hr. after training by again placing the rat in the lighted front compartment, and after a 60 secs. adaptation period, measuring the latency to enter the dark compartment. The test session ended when a rat entered the dark compartment or after 600 secs. had elapsed. Animals that failed to step through within 600 secs. were removed from the apparatus and a 600 secs. latency was recorded for them. The results are summarized in Table 4.

TABLE 4

| | Retention latency after 72 hours (in seconds) | | |
| --- | --- | --- | --- |
| Rats | double-distilled water | ($\pm$)-cis-isomer | (−)-cis-isomer |
| AF64A-treated | 181.4 ($\pm$53.3) | 407.9 ($\pm$72.1) | 563.5 ($\pm$23.6) |
| saline-treated | 593.3 ($\pm$47.5) | 478.2 ($\pm$65.7) | 474 ($\pm$61.3) |

Note: nine rats were treated in each group.

DISCUSSION

The net latencies of AF64A-treated groups, subsequently treated with either (−)- or ($\pm$)-cis-2-methylspiro(1,3-oxathiolan-5,3')quinuclidine were significantly longer ($p<0.005$ and $p<0.05$, respectively) than the group subsequently treated with double distilled water. Therefore, the retention of the step-through passive avoidance response of the AF64A-injected groups was significantly improved by both compounds, while the saline-treated groups did not change significantly when subjected to this subsequent treatment. This result provided an indication that administration of the (−)- or the ($\pm$)-cis-isomers can counter the cognitive impairment induced by the cholinergic neurotoxin AF64A.

While certain embodiments of the invention have been particularly described, it will be apparent to those skilled in the art that many modifications and variations may be made. The invention is accordingly not to be construed as restricted to such embodiments, rather its scope will be defined in accordance with the following claims.

We claim:

1. A pharmaceutical composition which comprises in combination:
   (i) at least one first active ingredient selected from the group consisting of (−)-cis-2-methylspiro(1,3-oxathiolan-5,3')-quinuclidine, and pharmaceutically compatible acid addition salts thereof;
   (ii) at least one second active ingredient selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor; and
   (iii) at least on inert diluent or carrier.

2. A pharmaceutical composition according to claim 1, which is in a form suitable for oral, rectal, parenteral or transdermal administration, or for administration by insufflation or nasal spray.

3. A pharmaceutical composition according to claim 2, which is in a form suitable for transdermal administration and which comprises as an additional component, a low molecular weight fatty acid.

4. A pharmaceutical composition according to claim 1, which is in unit dosage form.

5. A pharmaceutical composition according to claim 1, wherein said at least one first active ingredient is present in an amount in the range of about 0.5 to about 500 mg.

6. A pharmaceutical composition according to claim 5, wherein said amount lies within the range of about 5 to 100 mg.

7. A pharmaceutical composition according to claim 6 wherein said amount lies within the range of about 10 to 50 mg.

8. A pharmaceutical composition which comprises (−)-cis-2-methylspiro(1,3-oxathiolan-5,3')quinuclidine, or a pharmaceutically compatible acid addition salt thereof, and at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, prienzepine, N-methylatropine, N-butylscopolamine, scopolamine, clonidine, quanfamicine and Nerve Growth Factor.

9. A method for treating senile dementia of Alzheimer's type, which comprises coadministering to a patient in need thereof an effective dose of at least one compound selected from the group consisting of (−)-cis-2-methylspiro(1,3-oxathiolan-5,3')quinuclidine, and pharmaceutically compatible acid addition salts thereof, together with at least one compound selected from the group consisting of physostigmine, tetrahydroaminoacridine, choline, lecithin, piracetam, aniracetam, pramiracetam, oxiracetam, 4-aminopyridine, 3,4-diaminopyridine, somatostatin, pirenzepine, N-methylatropine, N-butylscopolamine, scopolamine, clonidine, quanfamicine and Nerve Growth Factor.

10. A method as in claim 9, wherein said coadministered compounds are in the form of a pharmaceutical composition, which comprises also at least one inert carrier or diluent.

11. A method as in claim 10, wherein said pharmaceutical composition is in a form suitable for oral, rectal, parenteral or transdermal administration, or for administration by insufflation or nasal spray.

12. A method according to claim 11, wherein said pharmaceutical composition is in a form suitable for transdermal administration, and said composition comprises, as an additional component, a low molecular weight fatty acid.

13. A method as in claim 9, wherein said at least one compound selected from the group consisting of (−)-cis-2-methylspiro(1,3-oxathiolan-5,3')quinuclidine, and pharmaceutically compatible acid addition salts thereof, is administered via the oral route in an amount which lies within the range of about 0.1 to about 60 mg./kg. body weight.

14. A method as in claim 13, wherein said amount lies within the range of about 0.5 to about 10 mg./kg. body weight.

15. A method as in claim 14, wherein said amount lies within the range of about 1 to 5 mg./kg. body weight.

16. A method as in claim 9, wherein said at least one compound selected from the group consisting of (−)-cis-2-methylspiro(1,3-oxathiolan-5,3')quinuclidine, and pharmaceutically compatible acid addition salts thereof, is administered via the parenteral route in an amount which lies within the range of about 0.01 to about 40 mg./kg. body weight.

17. A method as in claim 16, wherein said amount lies within the range of about 0.05 to about 5 mg./kg. body weight.

18. A method as in claim 17, wherein said amount lies within the range of about 0.1 to about 2 mg./kg. body weight.

* * * * *